(12) United States Patent
Sands et al.

(10) Patent No.: US 10,596,144 B2
(45) Date of Patent: *Mar. 24, 2020

(54) TREATING OR PREVENTING NEPHROGENIC DIABETES INSIPIDUS

(71) Applicant: Emory University, Atlanta, GA (US)

(72) Inventors: Jeff M. Sands, Atlanta, GA (US); Mitsi A. Blount, Atlanta, GA (US); Janet D. Klein, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,578

(22) Filed: Nov. 16, 2017

(65) Prior Publication Data

US 2018/0092876 A1 Apr. 5, 2018

Related U.S. Application Data

(63) Continuation of application No. 14/901,976, filed as application No. PCT/US2014/044483 on Jun. 27, 2014, now Pat. No. 9,827,222.

(Continued)

(51) Int. Cl.
*A61K 33/00* (2006.01)
*A61K 45/06* (2006.01)
(Continued)

(52) U.S. Cl.
CPC .......... *A61K 31/343* (2013.01); *A61K 31/155* (2013.01); *A61K 31/341* (2013.01);
(Continued)

(58) Field of Classification Search
CPC .. A61K 31/343; A61K 31/4965; A61K 45/06; A61K 31/405; A61K 31/427;
(Continued)

(56) References Cited

U.S. PATENT DOCUMENTS

| 5,864,381 A | 1/1999 | Neal |
| 9,827,222 B2 * | 11/2017 | Sands .................. A61K 31/155 |

(Continued)

FOREIGN PATENT DOCUMENTS

| WO | 2010100337 | 9/2010 |
| WO | 2015101609 | 7/2015 |
| WO | 2018144570 | 8/2018 |

OTHER PUBLICATIONS

Winder, Can Patients with Type 2 Diabetes Be Treated with AMPK Activators? (Year: 2008).*

(Continued)

*Primary Examiner* — Aradhana Sasan
*Assistant Examiner* — Quanglong N Truong
(74) *Attorney, Agent, or Firm* — Emory Patent Group

(57) ABSTRACT

In certain embodiments, the disclosure relates to methods of treating or preventing nephrogenic diabetes insipidus comprising administering an effective amount of a AMPK activator to a subject in need thereof, wherein In certain embodiments, the AMPK activator is metformin or salt thereof. In certain embodiments, the subject has been diagnosed with nephrogenic diabetes insipidus.

14 Claims, 4 Drawing Sheets

Related U.S. Application Data

(60) Provisional application No. 61/841,648, filed on Jul. 1, 2013.

(51) Int. Cl.

| | | |
|---|---|---|
| *A61K 31/155* | (2006.01) | |
| *A61K 31/341* | (2006.01) | |
| *A61K 31/343* | (2006.01) | |
| *A61K 31/405* | (2006.01) | |
| *A61K 31/427* | (2006.01) | |
| *A61K 31/549* | (2006.01) | |
| *A61K 31/4365* | (2006.01) | |
| *A61K 31/4965* | (2006.01) | |
| *A61K 31/7056* | (2006.01) | |
| *A61K 31/7076* | (2006.01) | |

(52) U.S. Cl.
CPC .......... *A61K 31/405* (2013.01); *A61K 31/427* (2013.01); *A61K 31/4365* (2013.01); *A61K 31/4965* (2013.01); *A61K 31/549* (2013.01); *A61K 31/7056* (2013.01); *A61K 31/7076* (2013.01); *A61K 33/00* (2013.01); *A61K 45/06* (2013.01)

(58) Field of Classification Search
CPC .. A61K 31/4365; A61K 33/00; A61K 31/549; A61K 31/7056; A61K 31/7076; A61K 31/341; A61K 31/155
See application file for complete search history.

(56) References Cited

U.S. PATENT DOCUMENTS

| | | | |
|---|---|---|---|
| 2004/0209847 | A1 | 10/2004 | Dasseux |
| 2005/0037450 | A1* | 2/2005 | York ................. C12N 9/00 435/21 |
| 2007/0149466 | A1 | 6/2007 | Milburn |
| 2009/0297497 | A1 | 12/2009 | Kishore |
| 2010/0137422 | A1 | 6/2010 | Yoo |
| 2010/0152215 | A1* | 6/2010 | Reaume ............. C07D 239/52 514/274 |
| 2011/0034505 | A1 | 2/2011 | Cravo |
| 2011/0236317 | A1* | 9/2011 | Cravo ................ C07D 251/10 424/9.2 |
| 2012/0029001 | A1 | 2/2012 | Procino |
| 2012/0071528 | A1 | 3/2012 | Khanna |
| 2014/0377380 | A1 | 12/2014 | Kishore |

OTHER PUBLICATIONS

Gruzman et al., Adenosine Monophosphate-Activated Protein Kinase (AMPK) as a New Target for Antidiabetic Drugs: A Review on Metabolic, Pharmacological and Chemical Considerations (Year: 2009).*

Guo et al., The adenosine derivative 2',3',5'-tri-O-acetyl-N6-(3-hydroxylaniline) adenosine activates AMPK and regulates lipid metabolism in vitro and in vivo (Year: 2011).*

Bardoux et al. Vasopressin contributes to hyperfiltration, albuminuria, and renal hypertrophy in diabetes mellitus: Study in vasopressin-deficient Brattleboro rats, Proc. Natl. Acad. Sci. USA vol. 96, pp. 10397-10402, 1999.

Efe et al. Metformin improves urine concentration in rodents with nephrogenic diabetes insipidus, JCI Insight. 2016;1 (11):e88409.

Ehealth, Metformin and Nephrogenic diabetes insipidus—from FDA reports, available at http://www.ehealthme.com/ds/metformin/nephrogenic%20diabetes%20insipidus/.

Eheath, Metformin and Polyuria—from FDA reports, available at http://www.ehealthme.com/ds/metformin/polyuria/.

Ehealth, How effective is Metformin Hydrochloride for Diabetes Insipidus?, available at http://www.ehealthme.com/cd/diabetes%20insipidus/metformin%20hydrochloride/.

Glucophage (metformin hydrochloride) Tablets product label 2017.

Gruzman et al. Adenosine Monophosphate-Activated Protein Kinase (AMPK) as a New Target for Antidiabetic Drugs: A Review on Metabolic, Pharmacological and Chemical Considerations, Rev Diabet Stud. 2009, 6(1):13-36.

Guo et al. The adenosine derivative 2',3',5'-tri-O-acetyl-N6-(3-hydroxylaniline) adenosine activates AMPK and regulates lipid metabolism in vitro and in vivo, Life Sciences 90 (2012) 1-7.

Iwasaki et al. Osmoregulation of Plasma Vasopressin in Diabetes Mellitus with Sustained Hyperglycemia, Journal of Neuroendocrinology, 1996, vol. 8, 755-760.

Kim et al. Antidiabetes and Antiobesity Effect of Cryptotanshinone via Activation of AMP-Activated Protein Kinase, Mol Pharmacol. 2007, 72(1):62-72.

Klein et al. Metformin, an AMPK activator, stimulates the phosphorylation of aquaporin 2 and urea transporter A1 inner medullary collecting ducts, Am J Physiol Renal Physiol. 2016, 310(10): F1008-F1012.

Monhart, Hypertension and chronic kidney diseases, core vasa, 55 (2013) e397-e402.

(NIDDK) National Institute of Diabetes and Digestive and Kidney Diseases, Diabetes Insipidus, available at https://www.niddk.nih.gov/health-information/kidney-disease/diabetes-insipidus.

Olesen et al. Vasopressin-independent targeting of aquaporin-2 by selective E-prostanoid receptor agonists alleviates nephrogenic diabetes insipidus, Proc Natl Acad Sci U S A. 2011, 108(31):12949-54.

Sands et al. Nephrogenic Diabetes Insipidus, Ann Intern Med. 2006;144:186-194.

Sands et al. Physiological insights into novel therapies for nephrogenic diabetes insipidus, Am J Physiol Renal Physiol 311: F1149-F1152, 2016.

Winder et al. Can Patients with Type 2 Diabetes Be Treated with AMPK Activators? Diabetologia. 2008, 51(10): 1761-1764.

* cited by examiner

TREATING OR PREVENTING NEPHROGENIC DIABETES INSIPIDUS

CROSS-REFERENCE TO RELATED APPLICATIONS

This application is a continuation of U.S. application Ser. No. 14/901,976 filed Dec. 29, 2015, which is the National Stage of International Application No. PCT/US2014/044483 filed Jun. 27, 2014, which claims the benefit of priority to U.S. Provisional Application No. 61/841,648 filed Jul. 1, 2013. The entirety of each of these applications is hereby incorporated by reference for all purposes.

STATEMENT REGARDING FEDERALLY SPONSORED RESEARCH OR DEVELOPMENT

This invention was made with government support under Grant DK041707 awarded by the National Institutes of Health. The government has certain rights in the invention.

BACKGROUND

Nephrogenic diabetes insipidus (NDI), a form of diabetes insipidus, is a disease characterized by the production of large quantities of dilute urine, which results from the inability of the kidney to respond to vasopressin, the primary hormone known to enable urine concentration. To avoid dehydration, those diagnosed with NDI must consume enough fluids to equal the amount of urine produced, which may be as high as 20 L of water per day. Some possible outcomes of the severe dehydration include low blood pressure, delirium, or mental retardation.

Vasopressin regulates urea transport through the activation of two cyclic AMP (cAMP) dependent signaling pathways: protein kinase A (PKA) and exchange protein activated by cAMP (Epac). Vasopressin acts by increasing the phosphorylation and apical plasma membrane accumulation of the UT-A1 urea transporter protein. Vasopressin has also been shown to regulate water transport via increasing phosphorylation and apical plasma membrane accumulation of the aquaporin-2 (AQP2) water channel. Thus, the inability of the kidney to respond to vasopressin manifests itself in irregularities in urine and water transport, leading to improper urine concentrations. See FIG. 1. See Sands et al., Epac regulation of the UT-A1 urea transporter in rat IMCDs, J Am Soc Nephrol, 20: 2018-2024, 2009 and Sands et al., Urea transport in the kidney, Compr Physiol, 1: 699-729, 2011.

Aside from lifestyle modifications that include increased water consumption and changes in diet, hydrochlorothiazide and amiloride are diuretics that manage the dehydration associated with NDI. Currently, there exist no therapies specifically targeted towards NDI. Therefore, there is a need for therapeutic treatments that address the kidney function in NDI cases.

Metformin has been used as a type II diabetes medication. See WO2012156298A1, EP2324853A1, EP2329848A1.

References cited herein are not an admission of prior art.

SUMMARY

In certain embodiments, the disclosure relates to methods of treating or preventing nephrogenic diabetes insipidus comprising administering an effective amount of a AMPK activator to a subject in need thereof, wherein In certain embodiments, the AMPK activator is metformin or salt thereof.

In certain embodiments, the subject has been diagnosed with nephrogenic diabetes insipidus.

In certain embodiments, the subject has symptoms of excessive urination and excessive thirst wherein urine of the subject does not contain glucose.

In certain embodiments, the subject is restricted from drinking water and an hourly increase in osmolality of urine of the subject is less than 30 mOsm/kg per hour for at least 3 hours.

In certain embodiments, the subject is not responsive vasopressin.

In certain embodiments, the AMPK activator is administered in combination with a thiazide, indomethacin, amiloride, or other diuretic.

In certain embodiments, the AMPK activator is administered in combination with lithium.

In certain embodiments, the AMPK activator is cryptotanshinone.

In certain embodiments, the AMPK activator is 5-aminoimidazole-4-carboxamide-1-beta-D-ribofuranoside, A-769662 [4-hydroxy-3-(2'-hydroxy-[1,1'-biphenyl]-4-yl)-6-oxo-6,7-dihydrothieno[2,3-b]pyridine-5-carbonitrile], D942 [5-(3-(4-(2-(4-Fluorophenyl) ethoxy)phenyl)propyl) furan-2-carboxylic acid], WS070117 [$O^{2'},O^{3'},O^{5'}$-tri-acetyl-N6-(3-hydroxylaniline)adenosine], PT1 [2-Chloro-5-[[5-[[5-(4,5-Dimethyl-2-nitrophenyl)-2-furanyl]methylene]-4,5-dihydro-4-ox-o-2-thiazolyl]amino]benzoic acid] or salts thereof.

DETAILED DISCUSSION

Figure 1:
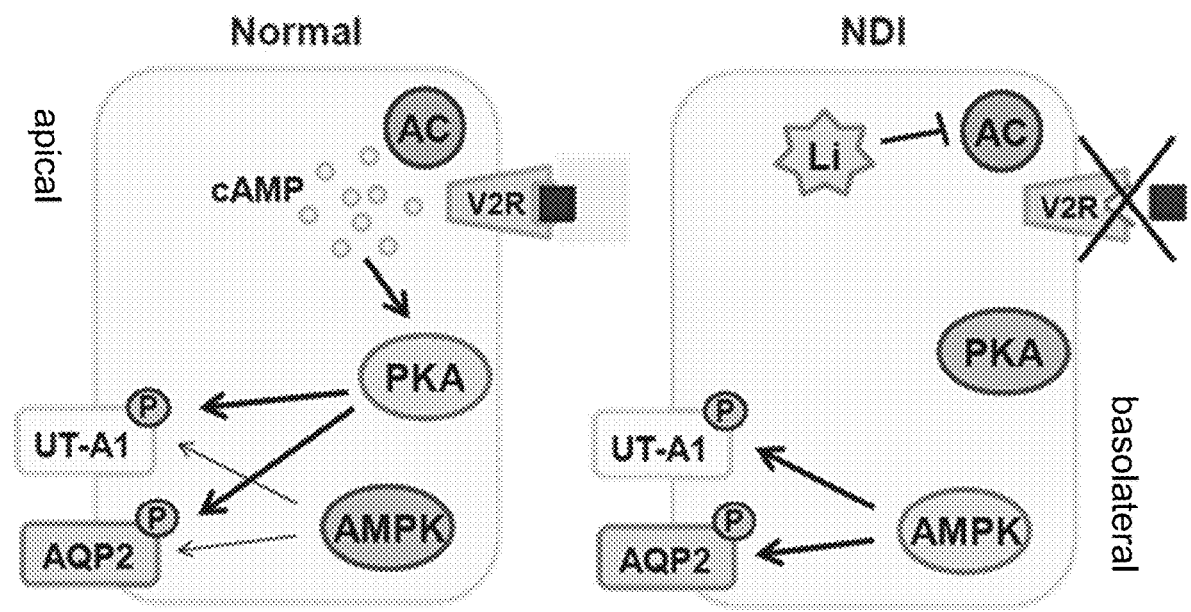
FIG. 1 shows that in the IMCD, vasopressin (red square) binds to the $V_2R$, resulting in increased cAMP via adenylyl cyclase (AC). Increased cAMP activates PKA, which in turn phosphorylates UT-A1 and AQP2. In NDI, when cAMP signaling is absent or reduced, AMPK provides an alternate kinase to phosphorylate AQP2 and UT-A1.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated. As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Nephrogenic Diabetes Insipidus

Nephrogenic diabetes insipidus (NDI), a form of diabetes insipidus, is a disease characterized by the production of large quantities of dilute urine, which results from the inability of the kidney to respond to vasopressin, the primary hormone known to enable urine concentration. To avoid dehydration, those diagnosed with NDI must consume enough fluids to equal the amount of urine produced, which may be as high as 20 L of water per day. This disclosure relates to a class of compounds that can treat or prevent nephrogenic diabetes insipidus (NDI). These compounds are classified as AMPK activators, since they enable the phosphorylation of both the UT-A1 and AQP2 proteins.

NDI may be congenital or acquired, with acquired NDI comprising the majority of cases. Acquired NDI is most commonly thought to stem from chronic lithium treatment, a classic treatment for bipolar disorders. Congenital NDI arises from mutations in the vasopressin receptor, $V_2R$, causing it to malfunction, or in the kidney water channel, resulting in a decreased ability to absorb water. Those undergoing chronic lithium treatment or possessing $V_2R$ mutations display no mutations in either the UT-A1 or AQP2 proteins. Thus, it is the inability to respond to vasopressin, and subsequently undergo phosphorylation, that leads to defects in urine concentration. (FIG. 1)

Some symptoms of NDI may be the production of large quantities of dilute urine and the subject experiencing excessive urination and excessive thirst wherein urine of the subject does not contain glucose. One test for the diagnosis of NDI includes restricting the subject from drinking water and finding that an hourly increase in osmolality of urine of the subject is less than 30 mOsm/kg per hour for at least 3 hours and the subject is not responsive to vasopressin.

AMPK Activator

In certain embodiments, the disclosure relates to a method of treating or preventing NDI comprising administering an AMPK activator. As used herein, the term "AMPK activator" refers to a substance that activates adenosine monophosphate kinase, AMPK. Some examples include cryptotanshinone, 5-aminoimidazole-4-carboxamide-1-beta-D-ribofuranoside, A-769662 [4-hydroxy-3-(2'-hydroxy-[1,1'-biphenyl]-4-yl)-6-oxo-6,7-dihydrothieno[2,3-b]pyridine-5-carbonitrile], D942 [5-(3-(4-(2-(4-Fluorophenyl) ethoxy) phenyl)propyl)furan-2-carboxylic acid], WS070117 [$O^{2'}$, $O^{3'},O^{5'}$-tri-acetyl-N6-(3-hydroxylaniline)adenosine], PT1 [2-Chloro-5-[[5-[[5-(4,5-Dimethyl-2-nitrophenyl)-2-furanyl]methylene]-4,5-dihydro-4-ox-o-2-thiazolyl]amino]benzoic acid] or salts thereof.

Prior to this invention, metformin (®Fortamet,®Glucophage,®Glumetza,®Riomet) was used as a treatment for type II diabetes.

Proguanil (®Paludrine) is another example of an AMPK activator and is used as a prophylactic antimalarial drug. See Carrington et al. A metabolite of paludrine with antimalarial activity. Nature 168: 1080, 1951.

Combination Therapies

In certain embodiments, the disclosure relates to method of treating or preventing NDI comprising administering an AMPK activator and a second active agent. In some embodiments, the second active agent is a diuretic or a P2Y purinergic receptor antagonist.

In certain embodiments, the disclosure relates to method of treating or preventing NDI comprising administering an AMPK activator and a diuretic. Some example diuretics include, but are not limited to, thiazide, indomethacin, and amiloride.

In certain embodiments, the disclosure relates to methods of treating or preventing NDI comprising administering an AMPK activator and a P2Y purinergic receptor antagonist. Examples of P2Y purinergic receptor antagonists include suramin, reactive blue 2, acid blue 129, acid blue 80, and pyridoxalphosphate-6-azophenyl-2',4'-disulfonic acid (PPADS). See U.S. Pat. Appl. No. 20090297497A1 for an example of an antagonist of the P2Y purinergic receptor used as a method of treatment of NDI.

Pharmaceutical Composition

In certain embodiment, the disclosure relates to pharmaceutical compositions comprising an AMPK activator disclosed herein and a second active agent, such as a diuretic or P2Y purinergic receptor antagonist. Some example diuretics include, but are not limited to, thiazide, indomethacin, and amiloride.

In certain embodiments, the pharmaceutical formulation is in the form of a pill, tablet, capsule, or gel or in the form of an aqueous saline buffer wherein the pharmaceutically acceptable excipient is a saccharide or polysaccharide.

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic fusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solution, Hank's solution, and other aqueous physiologically balanced salt solutions (see for example the most current editions of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM $MgCl_2$, 54 mg/l Tween 80, 10 mM Tris pH 8.5. Another typical composition is formulated in 10 mg/ml mannitol, 1 mg/ml HAS, 20 mM Tris, pH 7.2, and 150 mM NaCl.

The composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration include the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Viscosity enhancing agents include sodium carboxymethyl-cellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition may be administered to patients in an amount effective, especially to enhance an immune response in an animal or human organism. As used herein, the term "effective amount" refers to an amount sufficient to realize a desired biological effect. The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques. The administration may take place in a single dose or a dose repeated one or several times after a certain time interval.

In certain embodiments, the disclosure contemplates that an effective amount for a human subject is administering between 100 mg and 3,000 mg of metformin salt, or molar equivalent thereof daily or every two days for a duration of more than one week, two weeks, three weeks, one month, two months, six months or longer. In certain embodiments, the disclosure contemplates that an effective amount is administering between 100 mg and 480 mg daily or every other day. In certain embodiments, the disclosure contemplates that an effective amount is administering between 300 mg and 450 mg daily. In certain embodiments, the disclosure contemplates that an effective amount is administering between 400 mg and 1700 mg daily or every two or three days, or once a week. In certain embodiments, the disclosure contemplates that an effective amount is administering between 480 mg and 2,000 mg daily. Administration may be one, twice, or three times daily, e.g., single dose of 500 mg daily, single dose of 850 mg, 850 mg twice daily, or 850 my three times daily, single dose of 1,000 mg daily, single dose of 100 mg daily, single dose of 200 mg, single dose of 400 mg, 100 mg twice daily, or 200 mg three times daily. In one example, about 250 mg of metformin HCl is taken daily or every other day for more than two, ten, or thirty weeks. In one example, about 400 mg of metformin HCl is taken daily or every other day for more than two, ten, or thirty weeks. In one example, about 500 mg of metformin HCl is taken daily or every other day for more than thirty weeks. In one example, about 850 mg of metformin HCl is taken daily or every other day for more than thirty weeks. In one example, about 1,000 mg of metformin HCl is taken daily or every other day for more than thirty weeks.

In certain embodiments, for the administrations reported herein similar amounts converted to molar equivalents of the salts are contemplated. In certain embodiments, administrations may include an amount of less than 5%, 10%, or 20% variation by weight.

EXPERIMENTAL

AMPK is an energy-sensing kinase that can be stimulated by osmotic stress and hypoxia. It has never been studied in inner medulla, which is normally hypertonic and hypoxic. AMPK is a heterotrimeric kinase with one catalytic ($\alpha$) and two regulatory subunits ($\beta$ and $\gamma$). There are two different AMPK $\alpha$ subunits, $\alpha1$ and $\alpha2$; their expression is often tissue specific and their specific actions have only been studied in muscle. AMPK regulates several renal transport proteins in cortex and outer medulla, but its role in the inner medulla is unknown.

One approach towards the treatment of NDI would include a therapeutic that performs the function of vasopressin through increasing the phosphorylation and apical plasma membrane accumulation of both the UT-A1 and AQP2 proteins, lessening the severity of NDI. Thus, the therapeutic would behave similarly to vasopressin, circumventing a main issue associated with NDI. Although it is not intended that certain embodiments of the disclosure may be limited by any particular mechanism, it is believed that AMPK, independent of vasopressin, increases urine concentrating ability through increases in AQP2 and UT-A1, phosphorylation, apical plasma membrane accumulation, and function.

Figure 2:
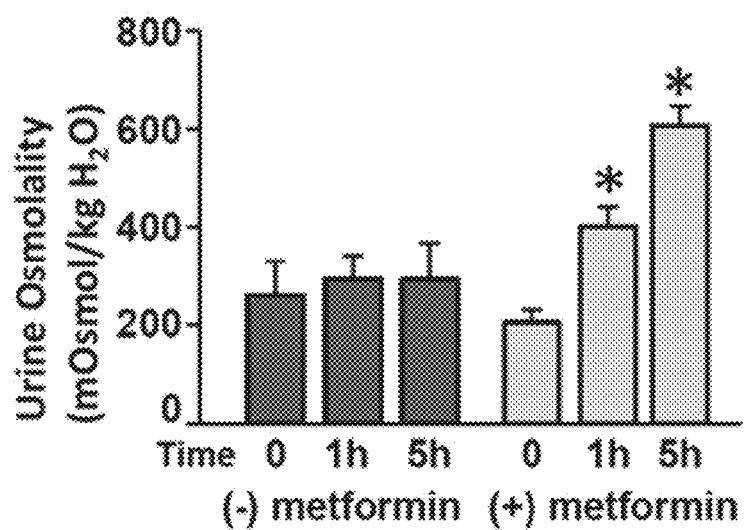
FIG. 2 illustrates the positive effect metformin has on urine osmolality in $V_2R$ knock-out mice.
Figure 3:
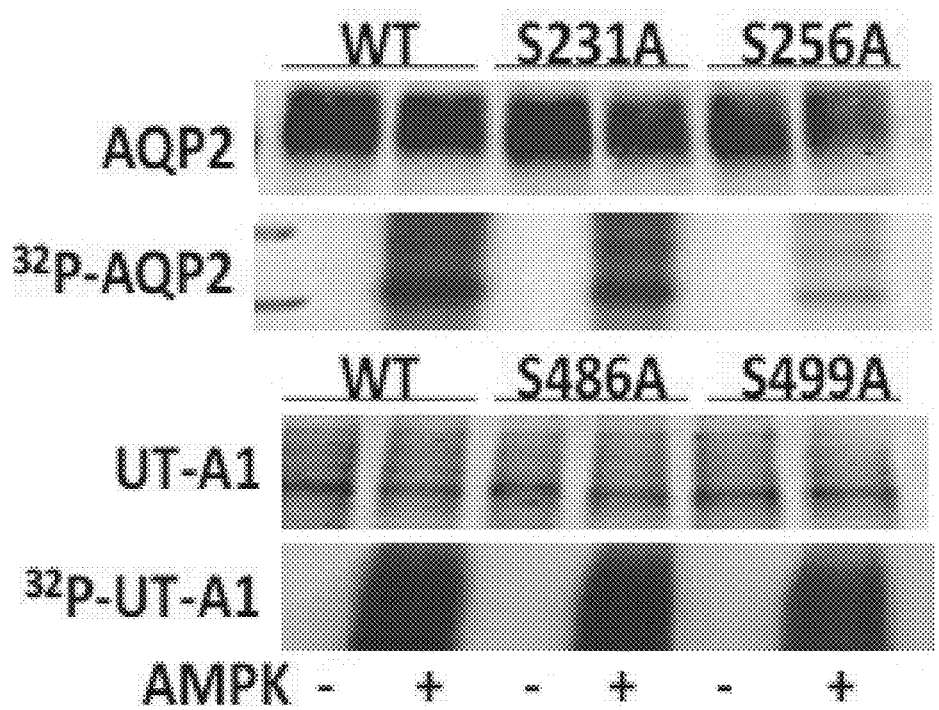
FIG. 3 illustrates AQP2 and UT-A1, wild type (WT) and with Ser-to-Ala mutations, undergo phosphorylation when treated with AMPK in vitro.
Figure 4:
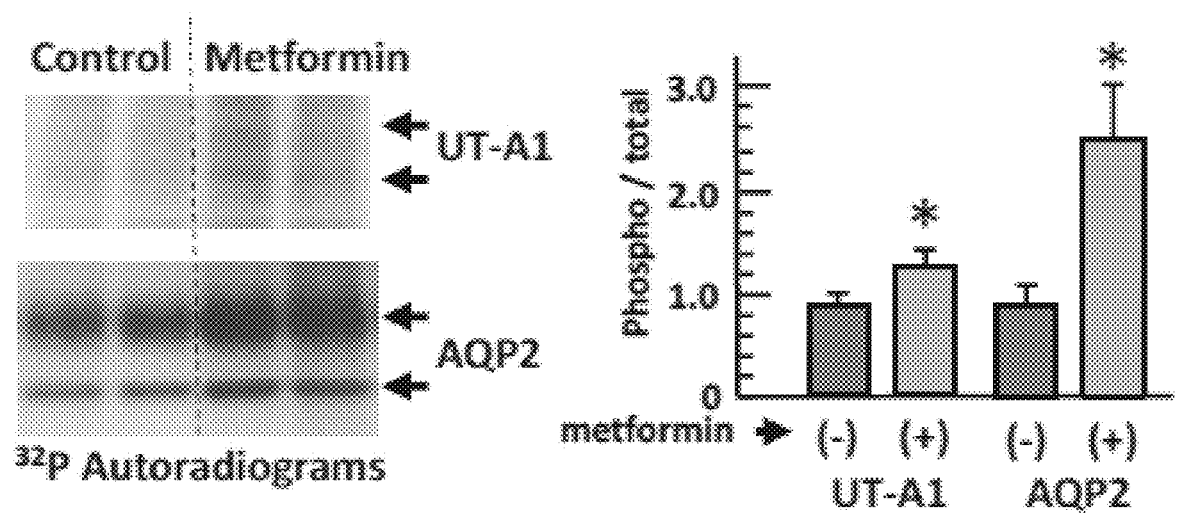
FIG. 4 illustrates UT-A1 and AQP2, in rat inner medullary tissue, undergo phosphorylation upon AMPK stimulation with metformin. *=p<0.05.

Preliminary data indicates AMPK phosphorylates both the UT-A1 and AQP2 proteins, both in vitro (FIG. 3) and in native rat IMCD suspensions (FIG. 4). Experimental data shows metformin, an AMPK activator, increases urine osmolality in mice lacking the vasopressin receptor, a mouse model of congenital NDI (FIG. 2). Thus, AMPK may mimic by which vasopressin increases urine concentrating ability.

Figure 5:
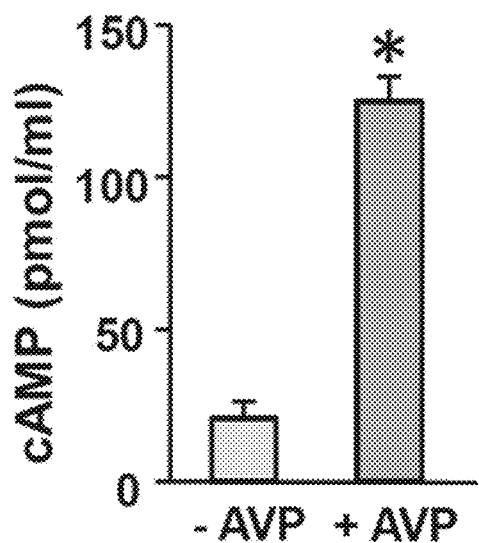
FIG. 5 illustrates cAMP in UT-A1-mIMCD3 cells after treatment with 1 μM vasopressin (AVP) for 10 min, *=p<0.05.
Figure 6:
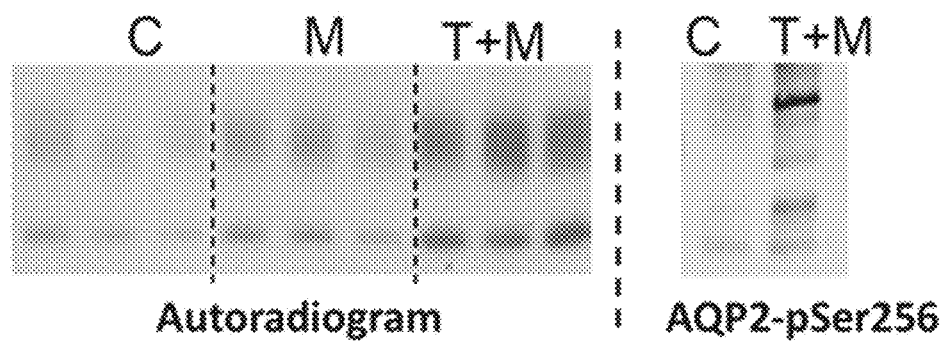
FIG. 6 illustrates AQP2 in rat inner medulla before (C) or after treatment with $10^{-4}$ M metformin (M) or $10^{-7}$ M tolvapten & metformin (T+M). Left: immune-precipitated 32P-AQP2; Right: phospho S256-AQP2.

Vasopressin increases cAMP in mIMCD3 cells (FIG. 5), suggesting these cells have a $V_2R$, the vasopressin receptor. Experimental data in native rat IMCDs in which tolvaptan, a $V_2R$ inhibitor, increased AQP2 phosphorylation, compared to metformin alone (FIG. 6, left). This finding suggests that the effect of metformin is greater when the $V_2R$ is inhibited.

Metformin increases pS256-AQP2 when the $V_2R$ is inhibited using tolvaptan (FIG. 6, right).

Figure 7:
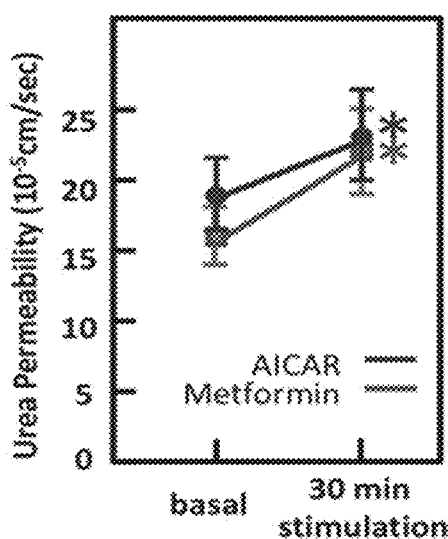
FIG. 7 illustrates urea permeability in perfused rat terminal IMCDs: response to AMPK stimulation by metformin (blue, n=4) or AICAR (red, n=4),*=p<0.05.
Figure 8:
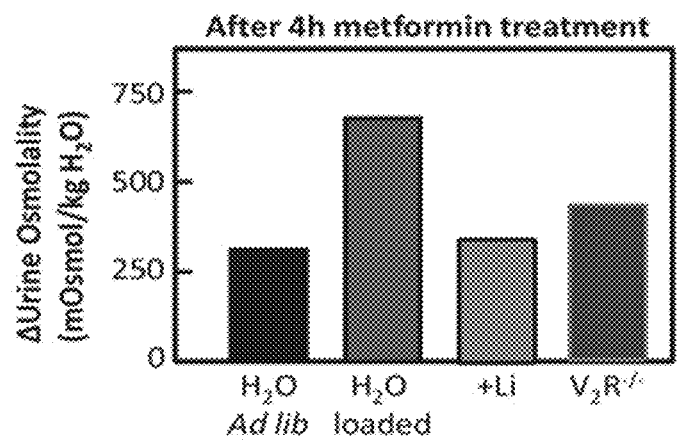
FIG. 8 illustrates the increase in urine Osm 4 h after IP injection of metformin. Rats with normal water (blue); water loaded for 1 week (red). Mice fed lithium for 14 days (green); $V_2R$−/− mice (brown).
Figure 9:
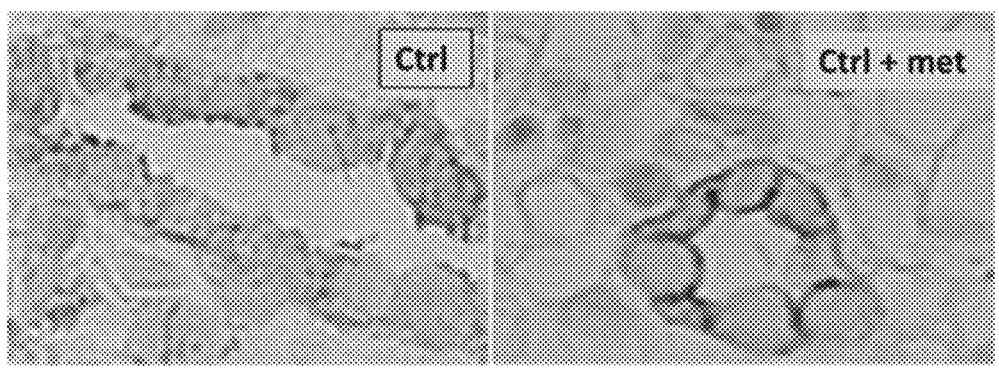
FIG. 9 illustrates AQP2 in IMCDs from control rats and rats treated (4 h) with 100 mg/kg metformin. 400×, HRP/Dab with hematoxylin stained nuclei.

In order to be useful therapeutically, an AMPK activator, such as metformin, should increase urine osmolality. Experimental data indicates that: 1) metformin increases urea permeability in perfused rat IMCDs, independent of vasopressin (FIG. 7); and 2) metformin increases urine osmolality in rats (FIG. 8), lithium-treated mice (FIG. 8), and $V_2R$ knock-out mice (FIGS. 2 and 8). These experiments indicate that AMPK activation results in functional changes in urine concentrating ability. Experiments also indicate that metformin (4 h, 100 mg/kg IP) increases apical plasma membrane AQP2 (FIG. 9).

The invention claimed is:

1. A method of preventing nephrogenic diabetes insipidus comprising administering an effective amount of an AMPK activator in combination with lithium to a subject in need thereof.

2. The method of claim 1, wherein the AMPK activator is metformin or salt thereof.

3. The method of claim 1, wherein the AMPK activator is 5-aminoimidazole-4-carboxamide-1-beta-D-ribofuranoside or salt thereof.

4. The method of claim 1, wherein the AMPK activator is 4-hydroxy-3-(2'-hydroxy-[1,1'-biphenyl]-4-yl)-6-oxo-6,7-dihydrothieno[2,3-b]pyridine-5-carbonitrile or salt thereof.

5. The method of claim 1, wherein the AMPK activator is 5-(3-(4-(2-(4-Fluorophenyl)ethoxy)phenyl)propyl)furan-2-carboxylic acid or salt thereof.

6. The method of claim 1, wherein the AMPK activator is O2',O3',O5'-tri-acetyl-N6-(3-hydroxylaniline)adenosine or salt thereof.

7. The method of claim 1, wherein the AMPK activator is 2-chloro-5-[[5-[[5-(4,5-Dimethyl-2-nitrophenyl)-2-furanyl]methylene]-4,5-dihydro-4-ox-o-2-thiazolyl]amino]benzoic acid or salts thereof.

8. A method of treating nephrogenic diabetes insipidus comprising administering an effective amount of an AMPK activator in combination with lithium to a subject in need thereof.

9. The method of claim 8, wherein the AMPK activator is metformin or salt thereof.

10. The method of claim 8, wherein the AMPK activator is 5-aminoimidazole-4-carboxamide-1-beta-D-ribofuranoside or salt thereof.

11. The method of claim 8, wherein the AMPK activator is 4-hydroxy-3-(2'-hydroxy-[1,1'-biphenyl]-4-yl)-6-oxo-6,7-dihydrothieno[2,3-b]pyridine-5-carbonitrile or salt thereof.

12. The method of claim 8, wherein the AMPK activator is 5-(3-(4-(2-(4-Fluorophenyl)ethoxy)phenyl)propyl)furan-2-carboxylic acid or salt thereof.

13. The method of claim 8, wherein the AMPK activator is O2',O3',O5'-tri-acetyl-N6-(3-hydroxylaniline)adenosine or salt thereof.

14. The method of claim 8, wherein the AMPK activator is 2-chloro-5-[[5-[[5-(4,5-Dimethyl-2-nitrophenyl)-2-furanyl]methylene]-4,5-dihydro-4-ox-o-2-thiazolyl]amino]benzoic acid or salts thereof.

* * * * *